United States Patent

Nystrom et al.

[11] Patent Number: 5,635,213
[45] Date of Patent: Jun. 3, 1997

[54] PHARMACEUTICAL FORMULATION

[75] Inventors: Christer Nystrom; Lennart Paalzow, both of Upsala; Sten-Magnus Aquilonius, Sigtuna, all of Sweden

[73] Assignee: Neopharma Production AB, Upsala, Sweden

[21] Appl. No.: 446,799

[22] PCT Filed: Nov. 29, 1993

[86] PCT No.: PCT/SE93/01029

§ 371 Date: May 30, 1995

§ 102(e) Date: May 30, 1995

[87] PCT Pub. No.: WO94/12153

PCT Pub. Date: Jun. 9, 1994

[30] Foreign Application Priority Data

Nov. 30, 1992 [SE] Sweden ................................ 9203594

[51] Int. Cl.$^6$ .................... A61K 9/14; A61K 31/24; A61K 31/135; A61K 31/195

[52] U.S. Cl. ................ 424/489; 514/534; 514/535; 514/561; 514/565; 514/567; 514/649

[58] Field of Search ........................ 424/489; 514/534, 514/535, 561, 565, 649

[56] References Cited

U.S. PATENT DOCUMENTS

| | | | |
|---|---|---|---|
| 4,356,824 | 11/1982 | Vazquez | 128/350 R |
| 4,826,875 | 5/1989 | Chiesi | 514/534 |
| 4,832,957 | 5/1989 | Dempski et al. | 424/469 |
| 4,840,799 | 6/1989 | Appelgren et al. | 424/493 |
| 4,863,962 | 9/1989 | Karoum et al. | 514/561 |
| 4,916,151 | 4/1990 | Bey et al. | 514/419 |
| 5,015,654 | 5/1991 | Al-Damluji | 514/402 |
| 5,266,332 | 11/1993 | Dong et al. | 424/473 |
| 5,326,572 | 7/1994 | Mehra et al. | 424/484 |
| 5,354,885 | 10/1994 | Milman et al. | 560/43 |

OTHER PUBLICATIONS

Miyazaki et al Chem. Pharm. Bull. 25(6):1186–1193 (1977) Chem. Abstr. 87:90670.

Kondo et al J. Pharm. Sci. 83(4):566–570 (1994) Chem. Abstr. 120:173209.

Bredberg et al Pharm. Res 11(4):549–535 Apr. 1994.

Bredberg et al Eur. J. Clin. Pharmacol. 45(2):117–122 (1993).

*Primary Examiner*—Shep K. Rose
*Attorney, Agent, or Firm*—Young & Thompson

[57] ABSTRACT

A pharmaceutical formulation for intraduodenal administration comprising at least one phamacologically active agent, with limited solubility in water and is dispersed in an aqueous carrier. According to the invention, the active agent has a particle size not exceeding 20 μm, and the aqueous carrier has a viscosity of at least 300 mPas, measured at a moderate shear rate.

9 Claims, 1 Drawing Sheet

PHARMACEUTICAL FORMULATION

The present invention relates to a pharmaceutical formulation for intraduodenal administration. More specifically, the invention relates to such a formulation comprising at least one pharmacologically active agent having a limited solubility in water. Still more specifically, the invention relates to such a formulation for the treatment of Parkinson's disease and comprising L-DOPA or an agent having similar properties. The term "limited solubility" is used in this patent application to refer to substances with low solubility in water and pharmacologically active substances for which the therapeutically active unit dose exceeds the solubility in water. The solubility of L-DOPA in water is about 5 mg/ml, and this patent covers drugs with both lower and higher solubility compared to L-DOPA.

L-DOPA (L-3,4-dihydroxyphenylalanine) has found a wide use for the treatment of patients suffering from Parkinson's disease, and good results are usually achieved by such a treatment. However, it is important in such a treatment that a stable level of the active agent is maintained in the patient's blood, and this has often been difficult to achieve in more conventional ways of administration, such as orally by tablets or capsules.

It has also been difficult to prepare liquid dosage forms of administration, as the compound L-DOPA has a very low solubility in water, so that large volumes of liquid have to be administered in order to give the patient an adequate dose. In several reports, the use of intraduodenal administration of aqueous solutions of drugs have shown several advantageous features as compared to oral administration of both tablets, suspensions and solutions (e.g. Watari et al., J. Pharmacokinet. Biopharm, Oct. 1983 11 (5), p. 529–545). Especially, the variation of drug plasma concentration was substantially reduced by using the intraduodenal route, mainly due to avoidance of the effect of variations in gastric emptying times. However, for drugs with limited solubility in water, the drug in suspended form is also an interesting possibility for intraduodenal administration. Furthermore, the compound L-DOPA is quite sensitive to oxidation and will decompose in solutions which are in contact with atmospheric air. These problems have practically ruled out the use of aqueous solutions of L-DOPA in therapy.

To eliminate the disadvantages mentioned, L-DOPA has been administered intraduodenally by an intraduodenal catheter through the abdominal wall of the patient, or by a naso-duodenal catheter. The formulation administered has then consisted of a suspension of L-DOPA in an aqueous carrier, thereby avoiding the problem of the low drug solubility. This method has given very good results as regards the maintaining of a stable level of L-DOPA in the patient's blood. But, to obtain a useful preparation still two further problems have to be considered. First, the risk of sedimentation of drug particles during storage and administration (referred to in this patent as the physical stability). Secondly, the chemical instability of L-DOPA due to oxidation.

Through the present invention, the drawbacks mentioned above are eliminated to a large extent. According to the invention a pharmaceutical formulation for intraduodenal administration is provided, comprising at least one pharmacologically active agent with a limited solubility in an aqueous carrier. What characterizes the invention is that the pharmacologically active agent has a particle size not exceeding 20 μm, and that the aqueous carrier has a viscosity of at least 300 mPas, measured at a moderate shear rate. These two characteristics have to be carefully controlled to produce an suspension with acceptable physical stability.

Preferably, the active agent has a particle size within the range 0.1 to 20 μm, and especially then between 0.1 and 5 μm.

The active agent is preferably L-DOPA and at least one of the agents, carbidopa or benserazide. It is preferably present in the formulation in an amount from 0.01 up to 20 weight percent, and especially then from 1 to 5 weight percent.

In a preferred embodiment of the invention, the pharmaceutical formulation is filled and stored under exclusion of oxygen.

Through the present invention it has become possible to achieve a highly advantageous therapeutic effect against Parkinson's disease by the intraduodenal administration of L-DOPA which has a very low solubility in water. The chemical stability of L-DOPA in an aqueous medium is also improved in a highly unexpected degree by this invention.

In the drawing, FIG. 1 shows a graph over the plasma concentration of L-DOPA as a function of the time after repeated administrations of tablets of a prior art formulation of L-DOPA. FIG. 2 shows the plasma concentrations of L-DOPA as a function of the time after intraduodenal infusion of an L-DOPA preparation according to the present invention.

The use of a very fine particle size for the pharmaceutical agent in the present invention must not be confused with the prior art use of pharmaceutical agents such as griseofulvin, in a finely divided form. This prior art use has only served to increase the rate of dissolution and as a consequence the bioavailability of the active agent, and in this case, a high viscosity of the formulation has not been desired, as it could result in reduced bioavailability. Thus, the object of using a very fine particle size in the formulations of the present invention is not to achieve an increased bioavailabitity, but to increase the physical stability of the formulation. In the present formulation this was achieved by the use of a very fine particulate quality of the drug in combination with the viscous aqueous medium. It was also unexpected that the chemical stability of L-DOPA was acceptable in this aqueous medium. The good chemical stability was achieved by the exclusion of atmospheric oxygen and the use of an aqueous medium of high viscosity.

In the work with the present invention the so-called volume diameter by weight as measured by the Coulter technique has been used. Furthermore, the particle size distribution may not only be calculated on a weight basis, but can also be expressed by number, length and surface, where the values will be lower than those given in the present description of the invention.

An alternative method of expressing particle fineness is the specific surface area, normally expressed as $m^2/g$. In the present case such measurements have been carried out by a gas permeability technique. These values may be said to correspond to the external or envelop surface area of the particles. Expressed in this manner, the maximum particle size given above (20 μm) would correspond to a value of at least 0.5 $m^2/g$. The interval 0.1 to 20 μm would correspond to an interval of 0.5 to 25 $m^2/g$. As stated above, the pharmacologically active agent should be suspended in an aqueous carrier having a viscosity of at least 300 mPas, measured at a moderate shear rate, and preferably being of a plastic or pseudoplastic nature. The plastic or pseudoplastic properties means that the vehicle or carrier will lower its viscosity during agitation, i.e. so-called shear thinning. This reduction in viscosity makes the liquid aqueous carrier more easy to pump through tubes with a small inner diameter of the type used in this invention. The degree of plasticity or pseudoplasticity can be expressed by several measures, according to well established and documented principles reported in the literature. Generally when a reference is made to a viscosity value in this invention, the value refers to the viscosity when the liquid carrier is moderately agitated, corresponding to a shear rate of less than approximately 500 $s^{-1}$ but higher than approximately 20 $s^{-1}$ i.e. the viscosity when the carrier is almost at rest. A typical shear rate representing such a condition at rest is 5 $s^{-1}$.

Such a carrier is usually an aqueous dispersion or solution of a pharmaceutically acceptable colloid, such as a water-soluble or water-swellable colloid of the carbohydrate or polysaccharide type or of a synthetic or semi-synthetic nature. As examples of such colloids may be mentioned cellulose ethers and other derivatives, such as methyl cellulose, carboxymethyl cellulose and sodium carboxymethyl cellulose, starches and starch derivatives, and plant gums and colloids such as Xantan gum, Guar gum, pectin, agar, alginates, dextran and other polysaccharides and derivatives thereof. Furthermore, water-soluble and water-swellable colloids of a synthetic or semi-synthetic origin may also be used, such as carbomers (carboxypolymethylenes, trade name Carbopol®), provided that they are pharmaceutically acceptable for the duodenal administering system.

The aqueous carrier should preferably have a viscosity at moderate agitation (shear rates between 20 and 500 $s^{-1}$) within the range from 300 to 5000 mPas and especially then within the range from 500 to 2000 mPas. For higher agitation intensities (shear rate higher than 500 $s^{-1}$) the viscosity should preferably be within the range from 10 to 1000 mPas, and especially then within the range from 50 to 500 mPas. A suitable viscosity may be obtained by adjusting the molecular weight of the colloid used into a suitable range. The molecular weight in its turn may be adjusted by selecting a suitable degree of polymerization, as is well-known to those skilled in the art. Furthermore, the viscosity may be adjusted by selecting a suitable concentration of the colloid in the aqueous system.

The preferred colloids to be used in the aqueous carrier are methyl cellulose, sodium carboxymethyl cellulose, carboxy-methyl cellulose and carbomers (carboxypolymethylenes, trade name Carbopol®).

The formulation of the invention is prepared by dispersing the active agent finely in the aqueous carrier using methods and apparatus which are well-known to those skilled in the art. It has turned out to be unexpectedly easy to achieve the necessary fine dispersion. This is a further important advantage of the invention.

The formulations of the invention may contain other additional agents which are well-known to those skilled in the art. As examples of such agents may be mentioned stabilizers, antioxidants, preserving agents and pH regulating agents. Such additional agents may be added to the formulations before, during or after the dispersion process.

The prepared formulations of the invention are subsequently dispensed into suitable containers for intraduodenal administration. Such containers may have a volume of about 100 ml, which in the evaluations performed has been a suitable volume of 2 weight percent L-DOPA for successful treatment of adult patients suffering from severe Parkinson's disease. The dose to be administered during a given period of time is determined by the physician on the basis of such criteria as the are and weight of the patient, the severity of the condition, and the like.

As has been stated above, it is an important feature of the invention that the formulations are prepared and stored under exclusion of oxygen. Thus, the formulation may be dispensed into bag-like containers of a plastic sheet material having a low permeability for oxygen. Furthermore, the filling of these containers may be carried out in such a manner that all air is first sucked out of the containers, after which the desired amount of the dispersion is pumped into the containers, and the containers are subsequently sealed. The containers are also provided with an outlet conduit, which is initially sealed, and is only opened immediately before the conduit is connected to a catheter for intraduodenal administration. By this arrangement, the container may also be emptied completely without any need for an air valve in the container.

The container with the formulation of the invention is usually placed in a type of cassette adapted to be carried by the patient. Such cassettes are previously known, and are provided with a pumping device for administering a metered amount of the formulation over a given time.

In a test, the stability was compared between a suspension of L-DOPA prepared in accordance with the present invention which had been stored under complete exclusion of air, and an aqueous suspension which had been stored in a container containing a certain amount of air. After ten weeks of storage, the amount of undegraded L-DOPA in the container which contained air had decreased to 75%, while no degradation could be observed of the L-DOPA which had been stored under complete exclusion of air.

Tests have also shown that it is the oxygen present in air above the suspension which is most responsible for the degradation. Oxygen dissolved in the aqueous phase only seems to be of minor importance for the degradation process.

In foregoing specification, the invention has been described mainly with reference to L-DOPA as the pharmacologically active agent. However, it is to be noted that the invention is not restricted to this agent only, but is applicable to all cases where a pharmacologically active agent with limited solubility in water or which is more stable in dispersed form is to be administered as a water based suspension.

The present invention is further described below by two examples, including graphs with clinical results. However, the possible range of design and formulation of the present invention is not by any means limited to the given examples.

EXAMPLE 1

In this example the active ingredients L-DOPA and carbidopa have been suspended in a viscous water solution of methyl cellulose and subsequently administered intraduodenally by a portable pump. The active ingredients L-DOPA and carbidopa were dry milled in a high speed, double rotating pin disc mill (Alpine 63C, Germany). The degree of fineness of the milled drugs was tested by a permeametric technique (Alderborn, Duberg and Nyström, Powder Technol. 41:49 (1985)), and found to be 1.3 $m^2/g$.

It should here be noted that also other milling techniques, well known to the expert in the field, could be used to obtain the high degree of particulate fineness needed.

The milled drugs were then suspended in a 1.8 weight percent water solution of methylcellulose-1500 (quality E) at room temperature (22°±2° C.). The viscosity of the methyl cellulose solution was determined at a shear rate of approximately 20 $s^{-1}$ to 1300 mPas. To achieve an adequate deagglomeration, the suspension was agitated by a magnetic stirrer and subsequently sonificated for two minutes. The concentrations of L-DOPA and carbidopa were 2.0 and 0.5 weight percent, respectively.

The well-dispersed suspension was then filled in cassettes (with a flexible plastic bag) of 100 ml. Prior to filling the bags are evacuated, resulting in a minute head space and thus oxygen content of the filled casssette. The cassettes were then stored in a refrigerator for no longer than 48 hours. This short storage time is however not a necessary requisite for the use of the present invention. On the contrary, it has been shown that chemical stability (mainly avoidance of oxidation of the active ingredients) could be maintained for longer than two months, without any significant degradation or even darkening of the suspension. Regarding the physical stability (sedimentation of suspended drug particles) it is related to the combination of drug particles fineness and the viscosity of the dispersion medium. For the present example no significant sedimentation was noted.

BRIEF DESCRIPTION OF THE DRAWINGS

The clinical effects of the present invention was compared with the conventional therapy with oral administration of Sinemet® tablets and Sinemet® depot tablets. Sinemet® is a registered trademark for a preparation of L-DOPA and carbidopa from Merck Sharp and Dohme, USA. The results are presented in FIGS. 1 and 2 of the drawing. The results show that the plasma concentrations of L-DOPA after administration of the tablet formulations varied substantially with high peak concentrations after each tablet intake followed by a rapid fall of the concentrations until intake of next dose. Pronounced variations in the blood concentration profiles between and also within individuals is a complicating factor in the treatment of Parkinson's disease. These variations are to a great deal caused by variations in gastric emptying times.

After intraduodenal administration of the present invention the plasma concentrations of L-DOPA were stable during the period of administration.

Figure 1:
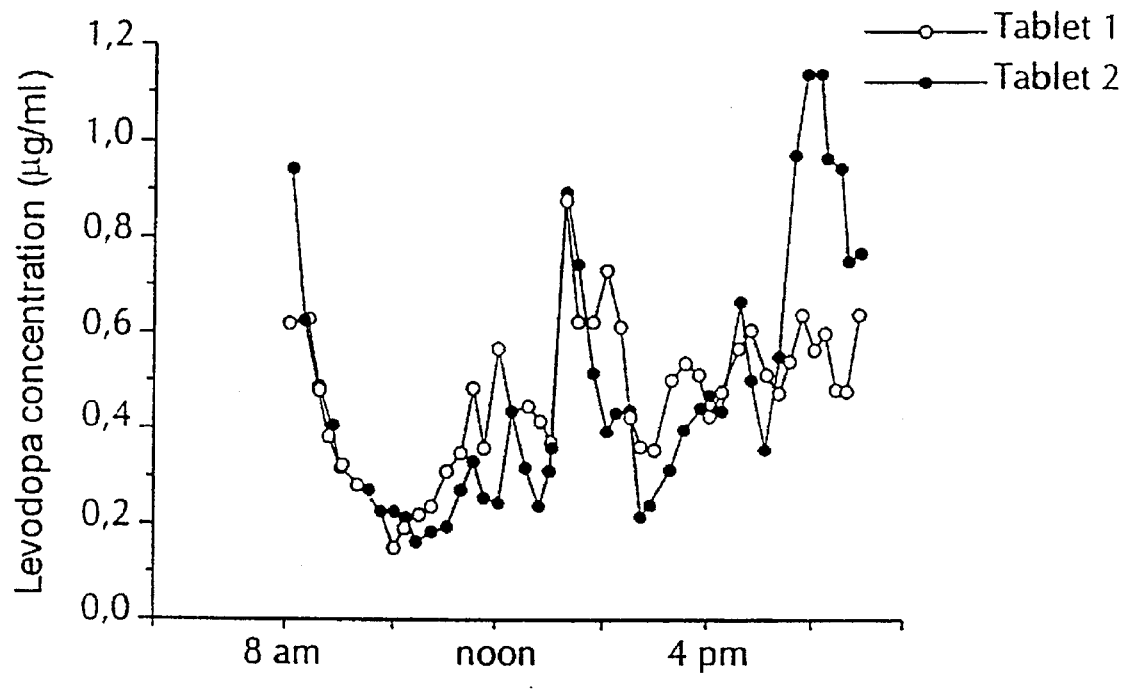
Figure 2:
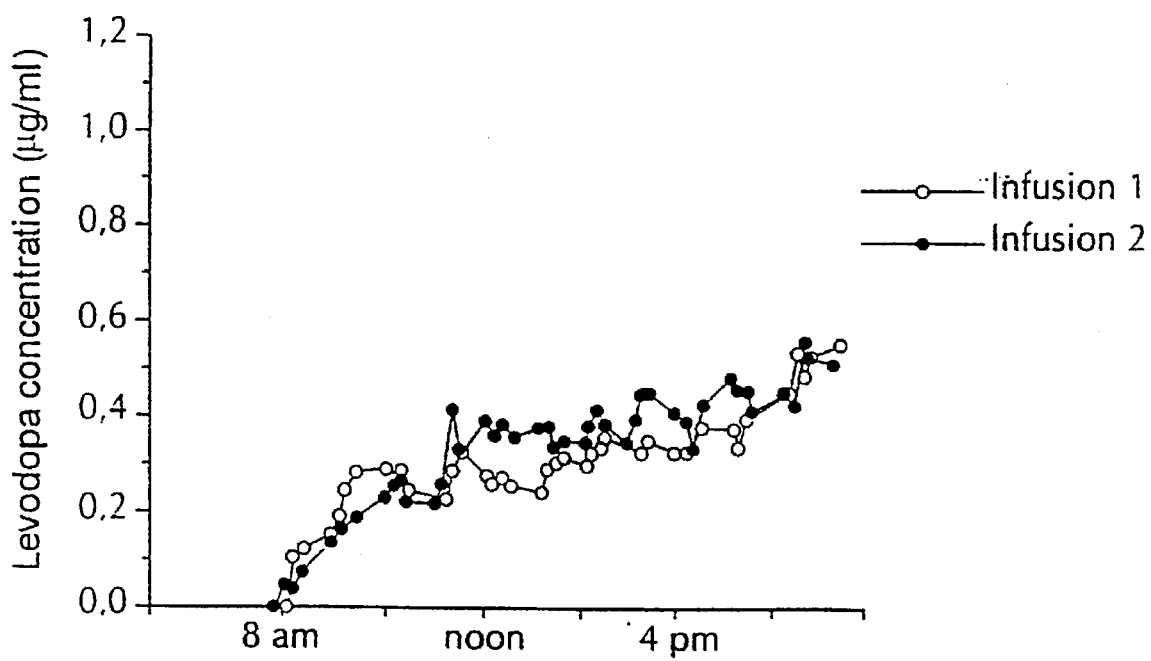

The patients mobility was better, with lower incidence of both hypomotility and hypermotility when L-DOPA was given as intraduodenal infusions during daytime compared to the patients optimized oral treatment with Sinemet® tablets.

EXAMPLE 2

To further illustrate the possibility to obtain a physically stable preparation, the use of a pesudoplastic aqueous carrier was tested.

The physical stability of a L-DOPA suspension, prepared from 0.3% w/w % Carbopol® 934P and 2 w/w % L-DOPA was investigated during 14 days. The suspension was prepared in a way similar to that in Example 1. Four cassettes of the suspension were prepared, and two cassettes were stored at 37° C. and the other two at room temperature. During the entire experiment period no agitation was applied, in order to simulate sedimentation during shelf storage of the suspension. Duplicate samples were collected and their concentrations of L-DOPA were determined. The results are given in Table 1. The concentrations of L-DOPA were assayed using an HPLC method with electrochemical detection.

TABLE 1

Physical stability of a 2% (w/w) of L-DOPA suspension with 0.3% (w/w) Carbopol ® 934P as carrier. Mean (SD)

| Day of assay | Temperature (°C.) | Conc L-DOPA % w/w (SD) |
|---|---|---|
| 0 |  | 1.87 (0.07) |
| 1 | 20 | 1.99 (0.12) |
|  | 37 | 1.99 (0.18) |
| 2 | 20 | 1.96 (0.05) |
|  | 37 | 1.99 (0.09) |
| 7 | 20 | 1.92 (0.05) |
|  | 37 | 1.92 (0.06) |
| 14 | 20 | 2.02 (0.04) |
|  | 37 | 2.06 (0.04) |

The result in Table 1 clearly show that no sedimentation of L-DOPA particles took place during the test period of 14 days. At the same time the suspension based on Carbopol® 934P was easy to pump through tubing of the same inner diameter as those used in the clinical application of this invention. In fact, Carbopol® 934P at concentrations much higher than 0.3% (w/w) could be pumped without any problems, although this concentration clearly was sufficient to maintain the L-DOPA in suspension. This combined effect of Carbopol® 934P and other plastic or pseudoplastic carriers is due to the so called shear thinning effect. When at rest these carriers posses a highly viscous structure while this structure is changed instantaneously upon application of agitation forces such as pumping.

These results demonstrate that by the use of the present invention it is possible to administer high doses of drugs with limited solubility using a small volume of an aqueous carrier (in this example 100 ml) of the formulated drug. The unexpectedly small variations in the plasma concentrations after intraduodenal infusion according to the present invention was achieved by using an extremely fine particulate quality of the drugs in combination with a high viscosity of the dispersion medium at rest.

Thus this invention not only facilitates the administration of high doses for long time infusions of drugs with limited solubulity in water. Administration of L-DOPA prepared with techniques described in this patent application also resulted in superior clinical effects in patients suffering from severe Parkinson's disease.

We claim:

1. In a method for intraduodenal administration of a pharmaceutical formulation, the improvement consisting essentially of the step of administering intraduodenally a pharmaceutical formulation comprising at least one pharmacologically active agent which has a low solubility in water and which is suspended in an aqueous carrier, characterized in that said active agent has a particle size not exceeding 20 μm, and that said carrier has a viscosity of at least 300 mPas, as measured at a moderate shear rate.

2. The method according to claim 1, characterized in that the active agent has a particle size in the range of 0.1 to 20 μm, preferably then 0.1 to 5 μm.

3. The method according to claim 1, characterized in that the active agent is L-DOPA and at least one of the agents carbidopa and benserazide.

4. The method according to claim 1, characterized in that it contains the active agent in an mount from 0.01 up to 20 weight percent, preferably then 0.1 to 5 weight percent.

5. The method according to claim 1, characterized in that the carrier is an aqueous dispersion or solution of a water-soluble or water-swellable colloid of the carbohydrate or polysaccharide type, or of a synthetic or semi-synthetic origin.

6. The method according to claim 5, characterized in that the carrier is of a plastic or pseudoplastic nature.

7. The method according to claim 6, characterized in that the carrier is a solution of methyl cellulose, sodium carboxymethyl cellulose, carboxymethyl cellulose or carboxypolymethylene, or a mixture of any of these materials.

8. The method according to claim 5, characterized in that the carrier has a viscosity, as measured at a moderate shear rate, in the range of 300 to 5000 mPas, preferably then 500 to 2000 mPas.

9. The method according to claim 1, containing L-DOPA and at least one of the compounds carbidopa and benserazide as the active agents for the treatment of Parkinson's disease.

* * * * *